United States Patent
Anastasio et al.

(10) Patent No.: US 10,598,612 B2
(45) Date of Patent: Mar. 24, 2020

(54) SINGLE-SHOT METHOD FOR EDGE ILLUMINATION X-RAY PHASE-CONTRAST TOMOGRAPHY

(71) Applicant: WASHINGTON UNIVERSITY, St. Louis, MO (US)

(72) Inventors: Mark Anthony Anastasio, St. Louis, MO (US); Yujia Chen, St. Louis, MO (US); Huifeng Guan, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 16/467,683

(22) PCT Filed: Feb. 1, 2018

(86) PCT No.: PCT/US2018/016401
§ 371 (c)(1),
(2) Date: Jun. 7, 2019

(87) PCT Pub. No.: WO2018/144705
PCT Pub. Date: Aug. 9, 2018

(65) Prior Publication Data
US 2019/0369033 A1    Dec. 5, 2019

Related U.S. Application Data (60) Provisional application No. 62/453,188, filed on Feb. 1, 2017.

(51) Int. Cl.
*G01N 23/00* (2006.01)
*G01N 23/046* (2018.01)
(Continued)

(52) U.S. Cl.
CPC ......... *G01N 23/046* (2013.01); *G01N 23/041* (2018.02); *G06T 11/008* (2013.01);
(Continued)

(58) Field of Classification Search
CPC ... G01N 23/046; G01N 23/041; G06T 11/008
See application file for complete search history.

(56) References Cited

U.S. PATENT DOCUMENTS 8,068,581 B2    11/2011  Boese et al.
8,805,037 B2    8/2014   Pack et al.
(Continued)

FOREIGN PATENT DOCUMENTS

WO    2009101569 A2    8/2009

OTHER PUBLICATIONS

International Search Report for International Application No. PCT/US2018/016401, dated May 10, 2018, 2 pages.
(Continued)

*Primary Examiner* — Dani Fox
(74) *Attorney, Agent, or Firm* — Armstrong Teasdale LLP (57) ABSTRACT

A method and systems of reconstructing a complex-valued X-ray refractive index distribution of an object having undergone X-ray phase-contrast tomography. The method includes acquiring at least one X-ray image of an object using an edge illumination X-ray phase-contrast tomography (EIXPCT) model, discretizing the model, jointly reconstructing the complex-valued refractive index distribution of the object using penalized least squares estimation of real and imaginary parts of the distribution, and solving the penalized least squares estimation using a batch gradient algorithm.

19 Claims, 10 Drawing Sheets

(51) Int. Cl.
*G01N 23/041* (2018.01)
*G06T 11/00* (2006.01)
(52) U.S. Cl.
CPC ............... *G01N 2223/60* (2013.01); *G06T 2207/10081* (2013.01); *G06T 2207/10116* (2013.01)

(56) References Cited

U.S. PATENT DOCUMENTS

| | | |
|---|---|---|
| 8,972,191 B2 | 3/2015 | Stampanoni et al. |
| 9,001,967 B2 | 4/2015 | Baturin et al. |
| 9,357,975 B2 | 6/2016 | Baturin et al. |
| 2010/0027739 A1 | 2/2010 | Lanza et al. |
| 2014/0016847 A1 | 1/2014 | Nett et al. |
| 2014/0037059 A1 | 2/2014 | Suft |
| 2014/0169524 A1 | 6/2014 | Sperl et al. |
| 2016/0063694 A1* | 3/2016 | Shi .................. G06K 9/4604 382/131 |

OTHER PUBLICATIONS

Written Opinion of the International Search Authority for International Application No. PCT/US2018/016401, dated May 10, 2018, 3 pages.
Chen, Y. et al. 2017.; "Single-shot edge illumination x-ray phase-contrast tomography enabled by joint image reconstruction." Optics Letters. vol. 42, Issue 3, pp. 619-622.
Morgan, K.S. et al. 2011. "Quantitative single-exposure x-ray phase contrast imaging using a single attenuation grid." Optics Express. vol. 19, No. 20, pp. 19781-19789.

\* cited by examiner

SINGLE-SHOT METHOD FOR EDGE ILLUMINATION X-RAY PHASE-CONTRAST TOMOGRAPHY

CROSS-REFERENCE TO RELATED APPLICATION

This application is a U.S. National Phase Application of PCT/US2018/016401, filed Feb. 1, 2018, which claims the benefit of priority to U.S. Provisional Patent Application Ser. No. 62/453,188, filed Feb. 1, 2017 and entitled SINGLE-SHOT METHOD FOR EDGE ILLUMINATION X-RAY PHASE-CONTRAST TOMOGRAPHY, the contents of which are hereby expressly incorporated by reference in their entirety.

STATEMENT REGARDING FEDERALLY SPONSORED RESEARCH & DEVELOPMENT

This invention was made with government support under Grant No. EB020604 awarded by National Institutes of Health and Grant No. CBET1263988 awarded by National Science Foundation. The U.S. government has certain rights in the invention.

TECHNICAL FIELD

The field of this invention relates generally to edge illumination X-ray phase-contrast tomography (EIXPCT), and more particularly, to a single-shot method for joint reconstruction of real- and imaginary-valued components of the refractive index distribution from a tomographic data set that contains only a single image acquired at each view angle.

BACKGROUND

Edge illumination X-ray phase-contrast tomography (EIXPCT) is an emerging X-ray phase-contrast tomography technique for reconstructing the complex-valued X-ray refractive index distribution of an object. Conventional EIXPCT image reconstruction methods typically contain two steps: phase-retrieval and image reconstruction. The phase-retrieval step generally requires two or more images acquired at each tomographic view angle. Multiple images contribute to prolonged imaging times and elevated radiation doses, which are both undesirable for in-vivo applications.

Additionally, single-shot EIXPCT methods have been presented. However, these methods generally require restrictive assumptions regarding the scanning geometry or the object (i.e., the object only contains one material). These methods may also require use of an energy-sensitive detector.

Accordingly, there is a need for a single-shot EIXPCT method that does not require restrictive assumptions of the scanning geometry or the object and does not require the use of an energy-sensitive detector.

BRIEF DESCRIPTION OF THE DISCLOSURE

In one aspect, a method of reconstructing a complex-valued X-ray refractive index distribution of an object having undergone X-ray phase-contrast tomography is provided. The method comprises acquiring at least one X-ray image of an object using an edge illumination X-ray phase-contrast tomography (EIXPCT) model, discretizing the EIX-PCT model, jointly reconstructing the complex-valued refractive index of the object using penalized least squares estimation, and solving the penalized least squares estimation using a batch gradient algorithm. The EIXPCT model is derived from a 2-dimensional Radon transform and the at least one X-ray image includes differential phase information. The penalized least squares estimation is of real and imaginary parts of the complex-valued refractive index distribution.

In another aspect, an X-ray system for conducting edge illumination X-ray phase-contrast tomography (EIXPCT) on an object is provided. The X-ray system includes an image processing system, an X-ray source, and an X-ray detector. The image processing system comprises at least one processor coupled to a memory. The image processing system, the X-ray source, and the X-ray detector are respectively communicatively coupled and configured to: acquire at least one X-ray image of an object using an edge illumination X-ray phase-contrast tomography (EIXPCT) model, discretize the EIXPCT model, jointly reconstruct the complex-valued refractive index of the object using penalized least squares estimation, and solve the penalized least squares estimation using a batch gradient algorithm. The EIXPCT model is derived from a 2-dimensional Radon transform and the at least one X-ray image includes differential phase information. The penalized least squares estimation is of real and imaginary parts of the complex-valued refractive index distribution.

In an additional aspect, an X-ray system for acquiring edge illumination X-ray phase-contrast tomography (EIX-PCT) images of an object is provided. The X-ray system comprises an X-ray source, a pre-sample mask, a detector mask, and an X-ray detector system. The acquired EIXPCT images of the object are processed by an image processing system coupled to the X-ray detector. The X-ray source, pre-sample mask, detector mask, the X-ray detector, and the image processing system are respectively communicatively coupled and configured in combination to: acquire at least one X-ray image of an object using an edge illumination X-ray phase-contrast tomography (EIXPCT) model, discretize the EIXPCT model, jointly reconstruct the complex-valued refractive index of the object using penalized least squares estimation, and solve the penalized least squares estimation using a batch gradient algorithm. The EIXPCT model is derived from a 2-dimensional Radon transform and the at least one X-ray image includes differential phase information. The penalized least squares estimation is of real and imaginary parts of the complex-valued refractive index distribution.

These and other features and advantages will be described in further detail below, with reference to the associated drawings.

DETAILED DESCRIPTION

As used herein, an element or step recited in the singular and preceded with the word "a" or "an" should be understood as not excluding plural elements or steps, unless such exclusion is explicitly recited. Furthermore, references to "example embodiment" or "one embodiment" of the present disclosure are not intended to be interpreted as excluding the existence of additional implementations that also incorporate the recited features.

Edge illumination X-ray phase-contrast tomography (EIXPCT) systems typically utilize two or more images acquired at each tomographic view angle to receive phase information from the images for image reconstruction. Embodiments of the methods and systems described herein utilize a single image (single-shot) acquired at each tomographic view angle for image reconstruction. Acquiring only a single-shot versus multiple shots per tomographic view angle exposes the object or subject being imaged to less ionizing radiation and enables a quicker imaging time.

Figure 1:
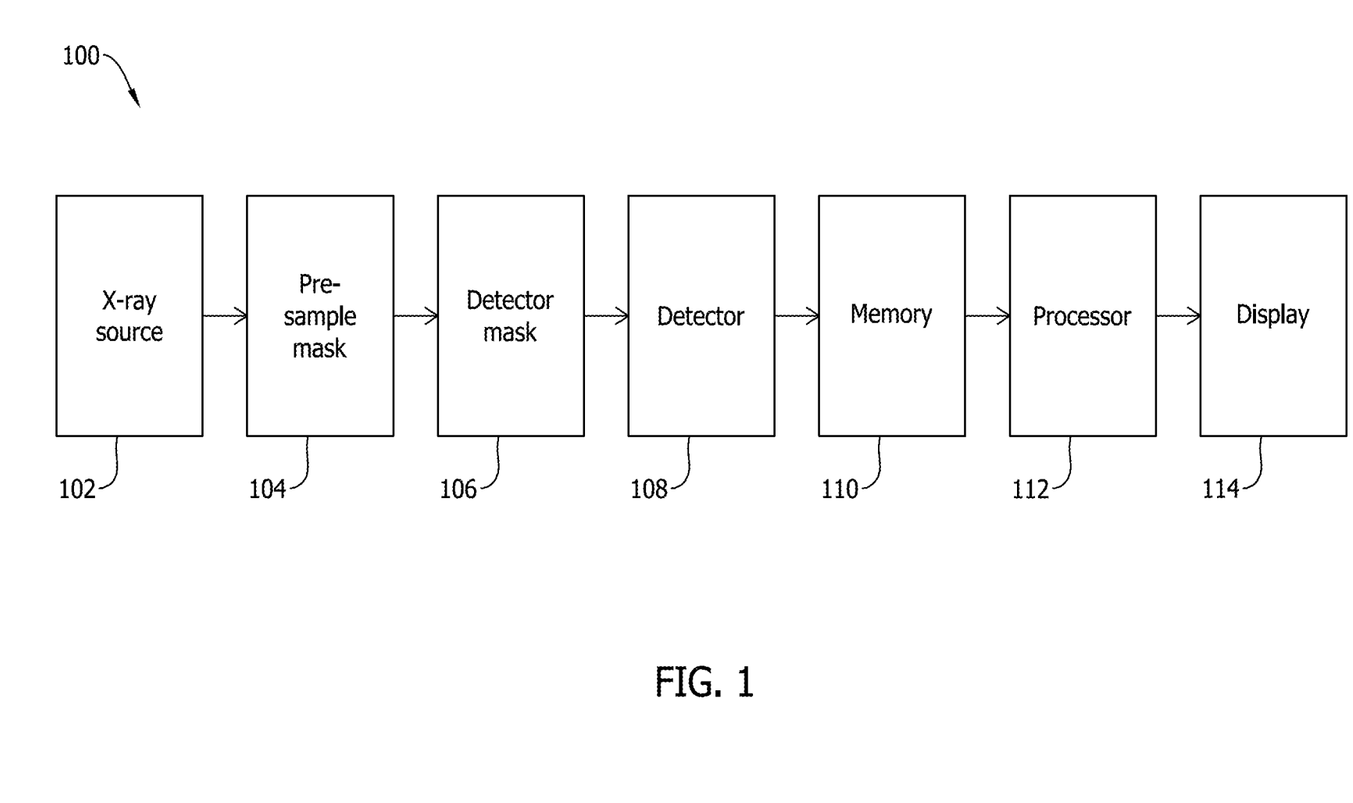
FIG. 1 is a block diagram of an exemplary X-ray system used in EIXPCT imaging.

FIG. 1 is a block diagram of an exemplary X-ray system 100 used in EIXPCT imaging. X-ray system 100 includes an X-ray source 102, a pre-sample mask 104, a detector mask 106, a detector 108, a memory 110, a processor 112, and a display 114. In some embodiments, the components of X-ray system 100 may be combined and/or separated in an alternative design to FIG. 1. X-ray system 100 may include additional components configured to provide support and/or additional capabilities for the components shown in FIG. 1.

In the exemplary embodiment, X-ray beams from X-ray source 102 pass through pre-sample mask 104 and detector mask 106 before reaching detector 108. X-ray source 102, pre-sample mask 104, detector mask 106, and detector 108 form or compose an X-ray image acquisition system 200 (shown in FIG. 2), described below. Memory 110, processor 112, and display 114 form or compose an image processing and reconstruction system. Memory 110 is coupled to detector 108. Image data from detector 108 is stored in memory 110. Processor 112 is coupled to memory 110. Stored image data from memory 110 is uploaded into processor 112. Processor 112 processes the image data and reconstructs one or more images to be displayed on display 114. In the exemplary embodiment, processor 112 carries out method 300, described below, and processor 112 may be any processor or computing device that can process EIXPCT image data. Display 114 may be any display screen or monitor that is suitable to display reconstructed EIXPCT images for a user, like, for example, a computer monitor coupled to processor 112.

Figure 2:
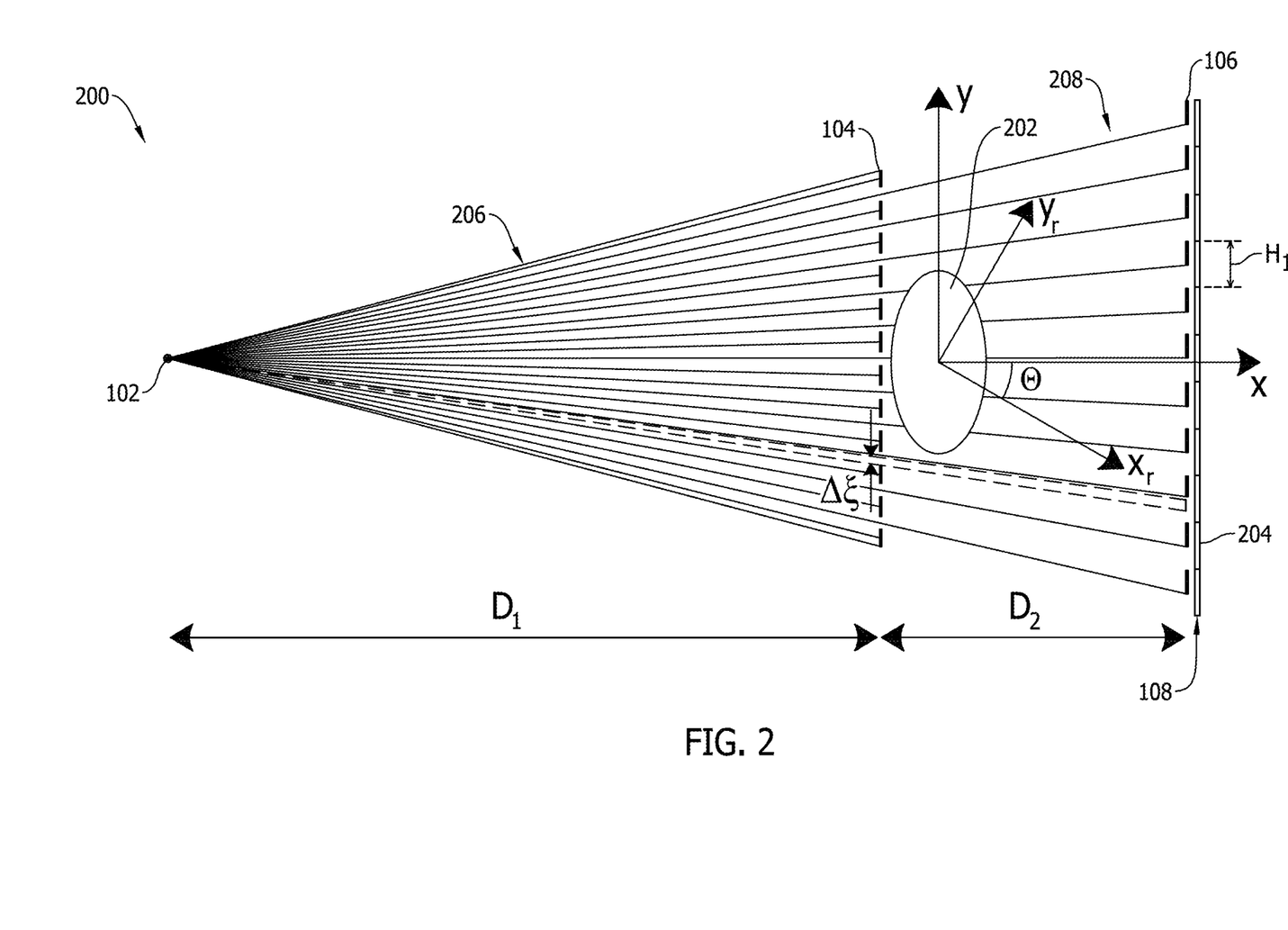
FIG. 2 is a schematic diagram of an exemplary X-ray system that may be used in EIXPCT image acquisition.

FIG. 2 is an example X-ray image acquisition system 200 for exemplary X-ray system 100, shown in FIG. 1. In the example embodiment, X-ray system 200 is an edge illumination X-ray phase-contrast tomography (EIXPCT) system for imaging an object 202. X-ray system 200 includes X-ray source 102, pre-sample mask 104, detector mask 106, detector 108, object 202, pixels 204, an X-ray beam 206, and incident X-ray beams 208. In some embodiments, the components of X-ray system 200 may be combined and/or separated in an alternative design to FIG. 2. X-ray image acquisition system 200 may include additional components configured to provide support and/or additional capabilities for the components shown in FIG. 2.

In the exemplary embodiment, object 202 is placed between X-ray source 102 and detector 108. Detector 108 includes a plurality of pixels 204, and each pixel 204 has substantially the same height $H_1$. Pre-sample mask 104 is placed between X-ray source 102 and object 202. Detector mask 106 is placed between object 202 and detector 108. Pre-sample mask 104 is configured to separate X-ray beam 206 when X-ray beam 206 passes through pre-sample mask 104. The separated X-ray beam becomes incident x-ray beams 208. Detector mask 106 is configured to block at least part of incident x-ray beams 208 from reaching pixels 204 of detector 108. In the exemplary embodiment, both pre-sample mask 104 and detector mask 106 are thin (i.e., 500 µm) and made of graphite. In alternate embodiments, pre-sample mask 104 and detector mask 106 can be made of any suitable material that separates X-ray beam 206 and blocks at least part of incident X-ray beams 208 from reaching detector 108, respectively. In the exemplary embodiment, pre-sample mask 104 and detector mask 106 are generally parallel to one another. The distance from X-ray source 102 to pre-sample mask 104 is a first distance $D_1$, and the distance from pre-sample mask 104 to detector mask 106 is a second distance $D_2$. First distance $D_1$ and second distance $D_2$ may be changed by moving pre-sample mask 104 along the x-axis, described below, before image acquisition is started.

Aperture offset $\Delta\xi$ is a predetermined distance that pre-sample mask 104 may be moved along the y-axis, described below, during image acquisition. In the exemplary embodiment, pre-sample mask 104 is moved by aperture offset $\Delta\xi$ along the y-axis during data acquisition by a piezoelectric motor (not shown). The piezoelectric motor moves pre-sample mask 104 very small distances (e.g., on the scale of μm) throughout the image acquisition process very accurately. In other embodiments, aperture offset $\Delta\xi$ is larger, and pre-sample mask 104 is moved a larger distance (e.g., cm) during image acquisition. Pre-sample mask 104 may be moved throughout image acquisition by any mechanical means that is able to move pre-sample mask 104 very small distances very accurately. Detector mask 106 is affixed to detector 108 during image acquisition. In the exemplary embodiment, aperture offset $\Delta\xi$ is one dimensional. In other embodiments, pre-sample mask 104 is moved in two dimensions (i.e., along the x- and y-axes), and aperture offset $\Delta\xi$ is two dimensional (i.e., L-shaped).

In the exemplary embodiment, coordinate r=(x,y) describes a stationary reference coordinate system with the origin of the reference system corresponding to an assumed origin of tomographic imaging of object 202. Rotating coordinate system $(x_r, y_r)$ is utilized to describe tomographic measurements. Rotating coordinate system $(x_r, y_r)$ is related to the stationary reference coordinate system (x,y) as $x_r$=x cos θ+y sin θ, $y_r$=y cos θ+x sin θ. Tomographic view angle θ is measured from the positive x-axis, $y_r$ denotes the detector coordinate, and the positive $x_r$-axis denotes the direction of incident X-ray beams 208.

In the illustrated embodiment, X-ray beam 206 and incident X-ray beams 208 have cone-beam geometry. In alternative embodiments, X-ray beam 206 and incident X-ray beams 208 have parallel-beam geometry. Method 300, described below, may be carried out on image data from any suitable X-ray beam geometry.

Figure 3:
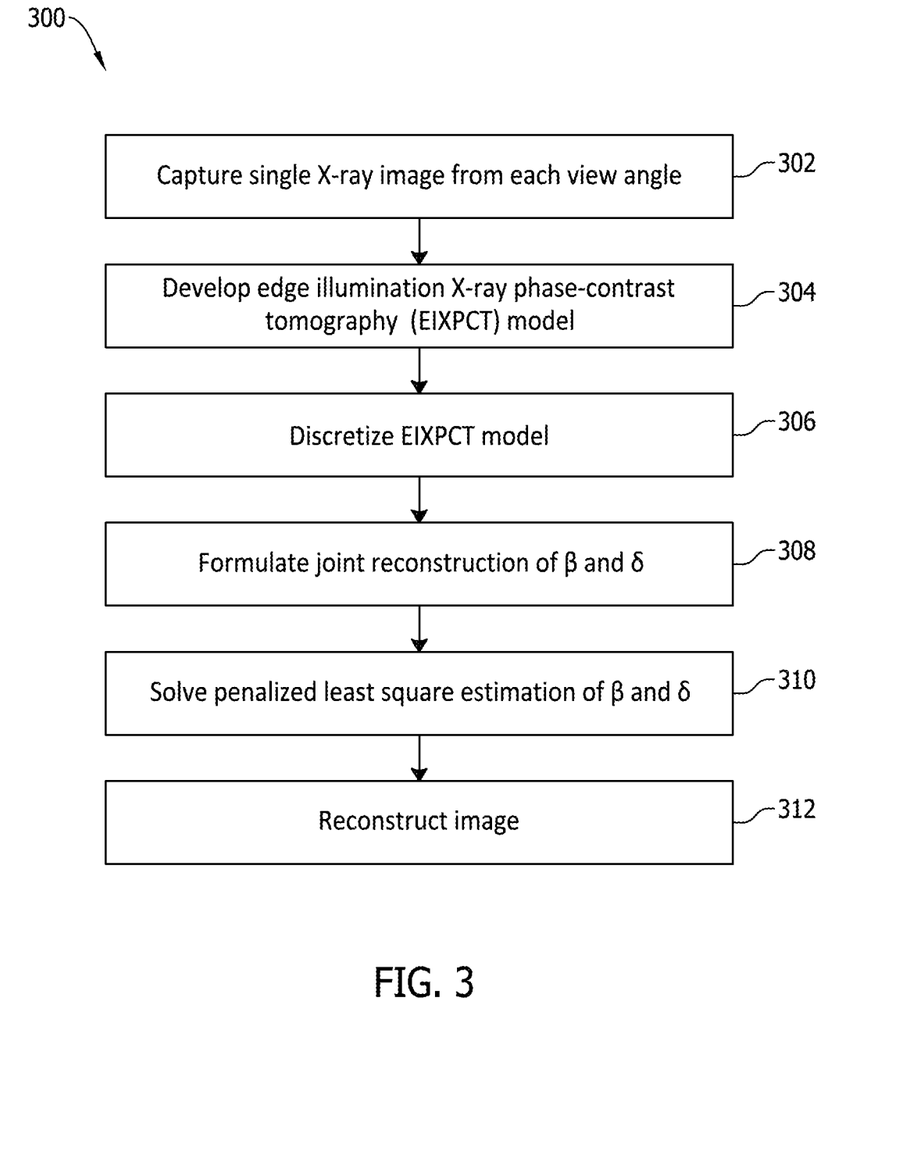
FIG. 3 is a flow diagram of an exemplary method of single-shot edge illumination X-ray phase-contrast tomography (EIXPCT)

FIG. 3 is a flow diagram of an exemplary method 300 for reconstructing a complex-valued X-ray refractive index using X-ray system 100 and X-ray image acquisition system 200, shown in FIGS. 1 and 2, respectively. The complex-valued refractive index distribution is denoted as n(r)=1−δ(r)+iβ(r), where i=$\sqrt{-1}$, δ is the unit difference of the real part of the refractive index, and β is the imaginary part. In the exemplary embodiment, method 300, described below, is carried out by processor 112 of X-ray system 100. Referring now to FIGS. 1 and 2, detector 108 captures 302 a single X-ray image from each tomographic view angle θ. An EIXPCT model is developed 304 from the single-shot X-ray images using a two-dimensional (2D) Radon transform operator, $\mathcal{H}$, that, when acting on β(r), includes differential phase information and is defined in Eq. 1:

$$p(\theta, y_r; \beta) = \mathcal{H} \beta(r) = \int_{L(y_r, \theta)} \beta(r) dx_r \quad \text{Eq. 1}$$

where the path of integration, $L(y_r, \theta)$, is parallel to $x_r$ and goes through $(0, y_r)$. The first-order derivative of the 2D Radon transform $\mathcal{D}$, with respect to detector coordinate y is defined in Eq. 2:

$$\mathcal{D}(\theta, y_r; \beta) \equiv \frac{\partial}{\partial y_r} p(\theta, y_r; \beta) = \frac{\partial}{\partial y_r} \int_{L(y_r, \theta)} \delta(r) dx_r \quad \text{Eq. 2}$$

Moving pre-sample mask 104 by aperture offset $\Delta\xi$ results in different parts of incident X-ray beams 208 falling onto insensitive areas of detector 108. In terms of these quantities and assuming monochromatic incident X-ray beams 208 with wavelength λ, the developed 304 EIXPCT model may be expressed as Eq. 3:

$$I(\theta, y_r; \beta, \delta) = \exp\left(-\frac{2\pi}{\lambda} p(\theta, y_r; \beta)\right) I_{TC}\left(\Delta\xi - \frac{D_2}{M} \mathcal{D}(\theta, y_r; \delta)\right) \quad \text{Eq. 3}$$

where $M=(D_1+D_2)/D_1$. $I_{TC}(\Delta\xi)$ represents an illumination curve that describes the relationship between the measured intensity and aperture position S when object 202 is absent. In the exemplary embodiment, $I_{TC}(\Delta\xi)$ is acquired by a separate calibration procedure. In the exemplary embodiment, aperture offset $\Delta\xi$ is fixed at a given tomographic view angle θ, because only a single image is recorded, but aperture offset $\Delta\xi$ may vary between tomographic view angles θ. Accordingly, notation $\Delta\xi_\theta$ for aperture offset is utilized. Having aperture offset $\Delta\xi_\theta$ varying between tomographic view angles θ, also known as having an alternating aperture position (AAP), distinguishes the method described in the current embodiment from other proposed single-shot methods that assume aperture offset is fixed at all tomographic view angles, also known as having a constant aperture position (CAP). It should be understood that both AAP and CAP data sets may be used in the exemplary method. In the exemplary embodiment, $(\theta, y_r; \delta)$ is small enough for Eq. 3 to be linearized by use of a Taylor expansion, defined in Eq. 4:

$$I(\theta, y_r; \beta, \delta) = \quad \text{Eq. 4}$$
$$\exp\left(-\frac{2\pi}{\lambda} p(\theta, y_r; \beta)\right) \left[I_{TC}(\Delta\xi_\theta) - \frac{D_2}{M} I'_{TC}(\Delta\xi_\theta) \mathcal{D}(\theta, y_r; \delta)\right]$$

where $I'_{TC}(\Delta\xi_\theta)$ is the first-order derivative of the illumination curve at aperture position $\Delta\xi_\theta$.

In the exemplary embodiment, developed 304 EIXPCT model, Eq. 4, is discretized 306 in order to formulate image reconstruction as a numerical optimization problem, described below. The discretized 306 version of the EIXPCT model is defined in Eq. 5:

$$[I(\beta, \delta)]_i = \exp\left(-\frac{2\pi}{\lambda}[H\beta]_i\right)\left[I_{TC}\left([\Delta\xi]_{\lceil\frac{i}{Q}\rceil}\right) - \frac{D_2}{M} I'_{TC}\left([\Delta\xi]_{\lceil\frac{i}{Q}\rceil}\right)[D\delta]_i\right] \quad \text{Eq. 5}$$

Referring to Eq. 5, i=1, 2, . . . , PQ and vectors $\beta=[\beta_{1,1}, \beta_{1,2}\ldots,\beta_{1,Nx},\beta_{2,1},\ldots,\beta_{Nx,Ny}]^T$ and $\delta=[\delta_{1,1},\delta_{1,2},\ldots,\delta_{1,Nx}, \delta_{2,1},\ldots,\delta_{Nx,Ny}]^T$ for all real number values of N represent the values of β(r) and δ(r) sampled at $N=N_xN_y$ vertices $r_{i,j}=(x_i,y_j)$ (i=1, 2, . . . , $N_x$ and j=1, 2, . . . , $N_y$) of a Cartesian grid. Q samples of the wavefield intensity corresponding to sampled values of $y_r$ are acquired at each of P tomographic view angles. Vector I(β,δ) for all real numbers for P and Q contains a lexicographical ordering of these values. Subscript i for vector values denotes the i-th component of the respective vector. Discrete representatives for the 2D Radon transform described in Eq. 1 and its first derivative described in Eq. 2 are denoted as H and D, respectively, for all real numbers of PQ×N. Quantity $\Delta\xi$ for all real numbers of N denotes the collection of aperture offsets employed at different tomographic view angles θ. Quantity $[\Delta\xi_\theta]_{[i/Q]}$ corresponds to the aperture offset $\Delta\xi$ employed at the tomographic view angle θ corresponding to the measurement $[I(\beta,\delta)]_i$, and $[i/Q]$ defines the smallest integer larger than $i/Q$.

Based on the discretized 306 EIXPCT model, joint reconstruction of β and δ may be formulated 308 as a numerical optimization problem. Penalized least squares of δ and β may be jointly determined, as shown in Eq. 6:

$$(\tilde{\beta},\tilde{\delta}) = \arg_{\tilde{\beta},\tilde{\delta}} \min \|I_m - I(\tilde{\beta},\tilde{\delta})\|^2 + R(\tilde{\beta},\tilde{\delta}) \quad \text{Eq. 6}$$

where $I_m$ and $I(\beta,\delta)$ denote measured intensity data and the intensity data simulated by use of Eq. 5 for a specified choice of δ and β, respectively. Penalty function $R(\tilde{\beta},\tilde{\delta})$ imposes regularization on the estimates of δ and β. This regularization of the estimates of δ and β is vital in jointly reconstructing and reduces noise in the process. In Eq. 6, the data fidelity term, $\arg_{\tilde{\beta},\tilde{\delta}} \min \|I_m - I(\tilde{\beta},\tilde{\delta})\|^2$, is non-convex and does not permit accurate image reconstruction. The penalty function was taken to be of the form $R(\tilde{\beta},\tilde{\delta}) = p_1 R_\beta(\tilde{\beta}) + p_2 R_\delta(\tilde{\delta})$, where $p_1$ and $p_2$ denote regularization parameters, and $R_\beta(\tilde{\beta})$ and $R_\delta(\tilde{\delta})$ are differentiable functions. Gradients of the objective function $f(\tilde{\beta},\tilde{\delta})$ with respect to the vectors $\tilde{\beta}$ and $\tilde{\delta}$ are given by Eqs. 7 and 8, respectively:

$$\nabla_{\tilde{\beta}} f(\tilde{\beta},\tilde{\delta}) = 2 I'^*_{\tilde{\beta}} (\tilde{\beta},\tilde{\delta}) - I_m) + \nabla_{\tilde{\beta}} R_\beta(\tilde{\beta},\tilde{\delta}) \quad \text{Eq. 7}$$

$$\nabla_{\tilde{\delta}} f(\tilde{\beta},\tilde{\delta}) = 2 I'^*_{\tilde{\delta}} (\tilde{\beta},\tilde{\delta}) - I_m) + \nabla_{\tilde{\delta}} R_\delta(\tilde{\beta},\tilde{\delta}) \quad \text{Eq. 8}$$

where $I'^*_{\tilde{\beta}}$ and $I'^*_{\tilde{\delta}}$ for all real numbers of N×PQ and denote the adjoint operator of the derivative of $I(\tilde{\beta},\tilde{\delta})$ with respect to $\tilde{\beta}$ and $\tilde{\delta}$, respectively. The adjoint operators applied to a small vector c for all real numbers of PQ can be computed as shown in Eqs. 9-11:

$$I'^*_{\tilde{\beta}} \varepsilon = \frac{2\pi}{\lambda} H^* x \text{ and } I'^*_{\tilde{\delta}} \varepsilon = -D^* y \text{ where} \quad \text{Eq. 9}$$

$$[x]_i = \left( I_{TC}\left([\Delta\xi]_{\left[\frac{i}{Q}\right]}\right) - \frac{D_2}{M} I'_{TC}\left([\Delta\xi]_{\left[\frac{i}{Q}\right]}\right)[D\tilde{\delta}]_i \right) \exp\left(-\frac{2\pi}{\lambda}[H\tilde{\beta}]_i\right) \varepsilon_i \quad \text{Eq. 10}$$

$$[y]_i = \frac{D_2}{M} I'_{TC}\left([\Delta\xi]_{\left[\frac{i}{Q}\right]}\right) \exp\left(-\frac{2\pi}{\lambda}[H\tilde{\beta}]_i\right) \varepsilon_i, i = 1, 2, \ldots, PQ. \quad \text{Eq. 11}$$

Finally, a batch gradient algorithm designed for edge illumination data sets is used to solve 310 the penalized least square estimation of δ and β, also known as joint reconstruction of δ and β, shown in Eq. 6. An example of a batch gradient algorithm is shown below:

| Algorithm I |
| --- |
| 1: Calibrate the illumination curve |
| 2: Read in measured data I |
| 3: Initialization: $\tilde{\beta}^{(0)} \leftarrow 0$; $\tilde{\delta}^{(0)} \leftarrow 0$; $k \leftarrow 0$ |
| 4: while stopping criterion is not satisfied do |
| 5: $k \leftarrow k + 1$ |
| 6: Calculate the intensity data $I(\tilde{\beta}^{(k)}, \tilde{\delta}^{(k)})$ |
| 7: Compute cost $\|I_m - I(\tilde{\beta}^{(k)}, \tilde{\delta}^{(k)})\|^2 + R(\tilde{\beta}^{(k)}, \tilde{\delta}^{(k)})$ |
| 8: $d_\beta \leftarrow -\nabla_\beta \|I_m - I(\tilde{\beta}^{(k)}, \tilde{\delta}^{(k)})\|^2 + p_1 \nabla_\beta R_{TV}(\beta^{(k)})$   ▷ $\nabla_\beta$ denotes the derivative w.r.t. β |
| 9: $d_\delta \leftarrow -\nabla_\delta \|I_m - I(\tilde{\beta}^{(k)}, \tilde{\delta}^{(k)})\|^2 + p_2 \nabla_\delta R_{TV}\delta^{(k)})$   ▷ $\nabla_\delta$ denotes the derivative w.r.t δ |
| 10: $(\tilde{\beta}^{(k+1)}, \tilde{\delta}^{(k+1)}) \leftarrow (\tilde{\beta}^{(k)}, \tilde{\delta}^{(k)}) + \tau(d_\beta, d_\delta)$   ▷ τ is the step size obtained by a line search method |

Example batch gradient algorithm, Algorithm 1, calibrates illumination curve $I_{TC}(\Delta\xi_0)$, reads in measured data I, initializes vectors $\tilde{\beta}$ and $\tilde{\delta}$ and starting coefficient k, and iterates through specific criterion to be satisfied for objective function $f(\tilde{\beta},\tilde{\delta})$ value to fall below a predetermined threshold. Algorithm 1 stops iteration through the criterion when the objective function $f(\tilde{\beta},\tilde{\delta})$ value falls below the specified threshold.

In the exemplary embodiment, images are reconstructed 312 using Algorithm 1. Penalty functions $R_\beta(\tilde{\beta})$ and $R_\delta(\tilde{\delta})$ are specified as a smoothed version of the total variation semi-norm. Suitable values of regularization parameters $p_2$ and $p_1$ are manually determined and fixed for use with constant aperture position (CAP) and/or alternating aperture position (AAP) data sets. When implemented on processor 112, Algorithm 1 constructs estimates of δ and β and therefor reconstructs images of object 202 from each image taken from each tomographic view angle θ with the differential phase information encoded in the measured X-ray wave intensity $I(\theta, y_r; \beta, \delta)$.

EXAMPLES

The following example demonstrates various aspects of the disclosure.

Example 1: Computer-Simulation of Joint Reconstruction of β and δ

The following examples illustrate the feasibility of achieving accurate joint reconstruction (JR) of a unit difference of imaginary part of refractive index β and real part δ from idealized noiseless measurements by use of Algorithm 1 (described above).

Figure 4A:
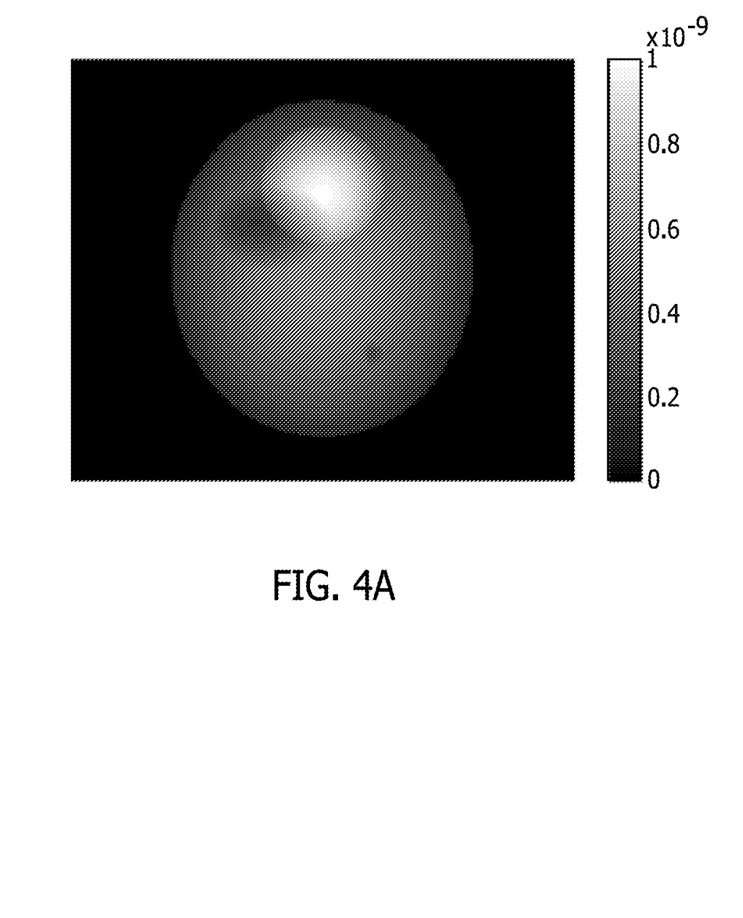
FIG. 4A is an image of numerical phantom utilized to represent penalized least squares estimation of $\beta$.
Figure 4B:
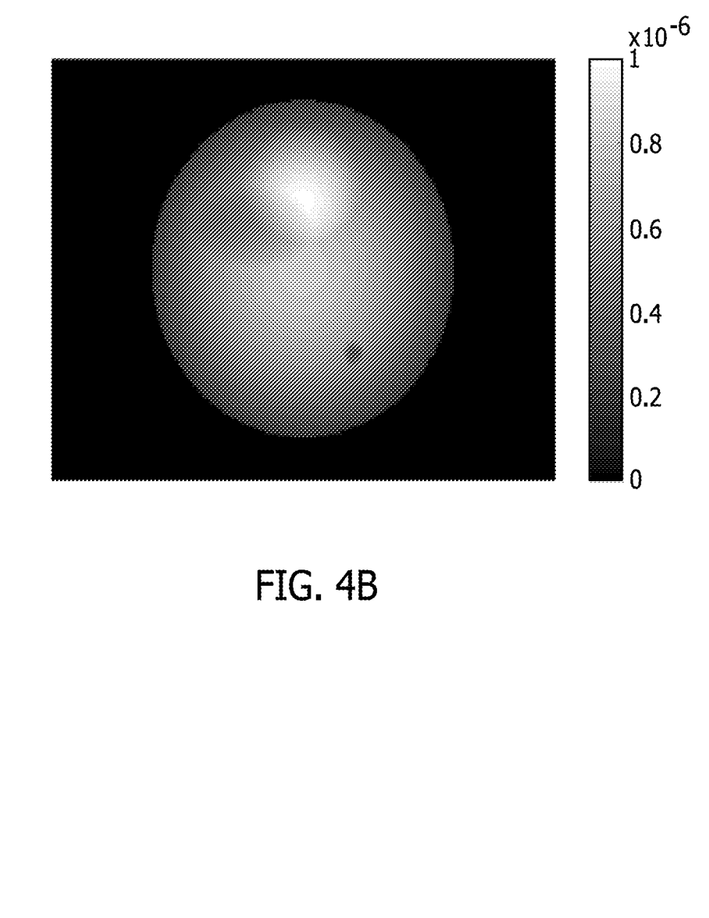
FIG. 4B is an image of numerical phantom utilized to represent penalized least squares estimation of $\delta$.

FIGS. 4A and 4B show the numerical phantoms that were employed to represent β and δ, respectively. The phantoms both contained 256×256 pixels of size 100 μm×100 μm and multiple materials, and the values of 3 and 6 were chosen to represent soft tissue. Noiseless simulated intensity data was computed by using Eq. 3, described above. At each tomographic view angle θ, 400 samples of the wavefield intensity were recorded along the detector array. The illumination curve was modeled after experimental measurements and was fitted by a Gaussian distribution, $I_{TC}=0.13+0.87 \exp(-\Delta\xi^2/1.84\times10^{-10})$, where the unit for aperture offset Δξ was m and $I_{TC}$ had an arbitrary unit. The assumed imaging parameters were: $D_1=1.6$ m, $D_2=0.4$ m, and $\lambda=10^{-10}$ m. Aperture offset Δξ was chosen by selecting aperture position Δξ with the steepest derivative in the illumination curve. Two candidates were Δξ=9.6 μm and Δξ=−9.6 μm.

Figure 5A:
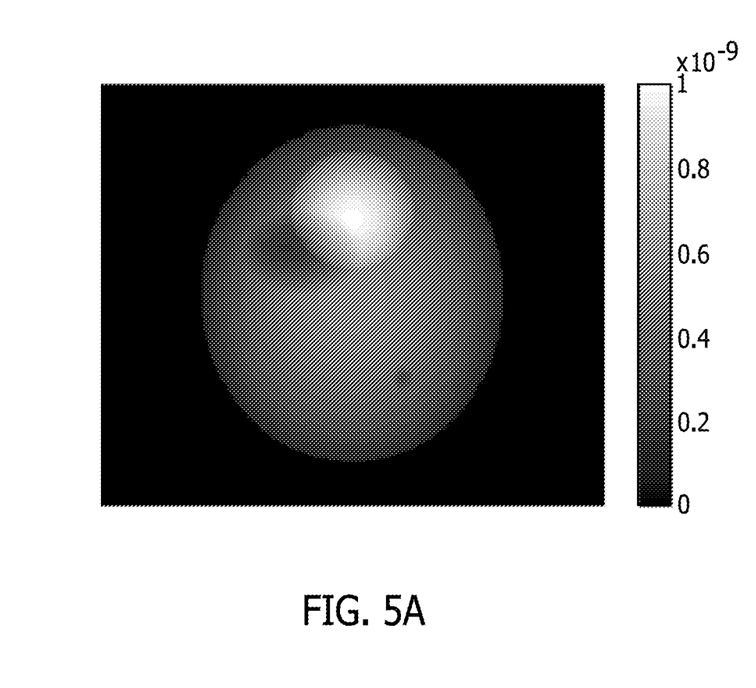
FIG. 5A is a computer-simulation result of reconstructed image of β, corresponding to a constant aperture position (CAP)
Figure 5B:
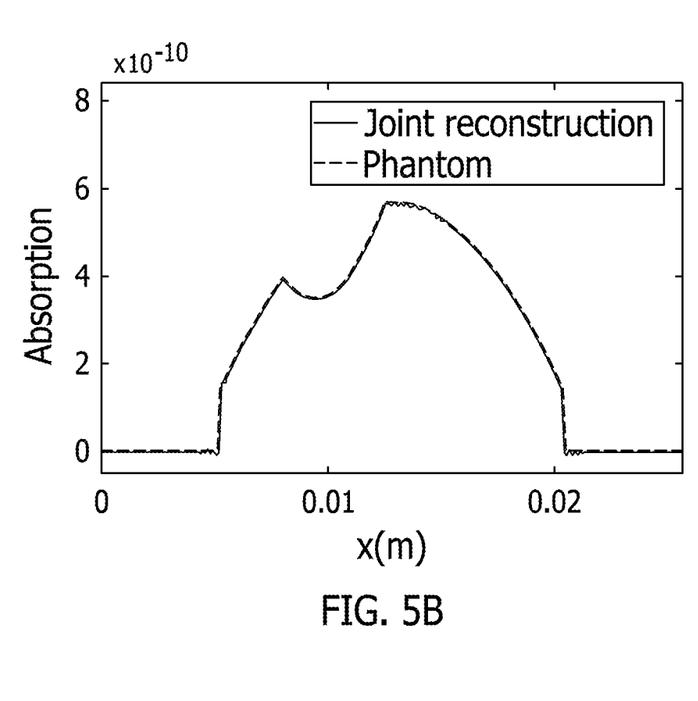
FIG. 5B is a graph of line profiles through the reconstructed image shown in FIG. 5A and corresponding true phantom shown in FIG. 4A.
Figure 5C:
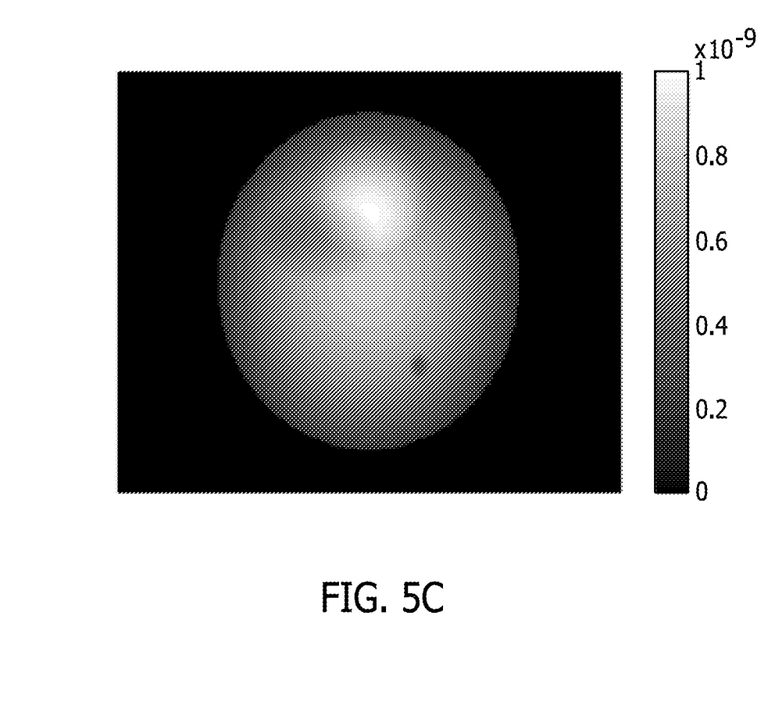
FIG. 5C is a computer-simulation result of reconstructed image of δ, corresponding to a CAP.
Figure 5D:
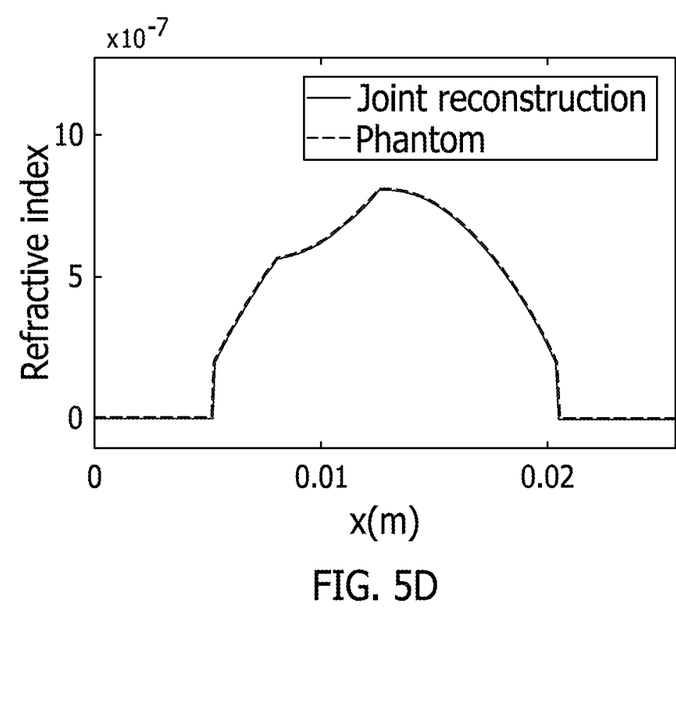
FIG. 5D is a graph of line profiles through the reconstructed image shown in FIG. 5C and corresponding true phantom shown in FIG. 4B.
Figure 6A:
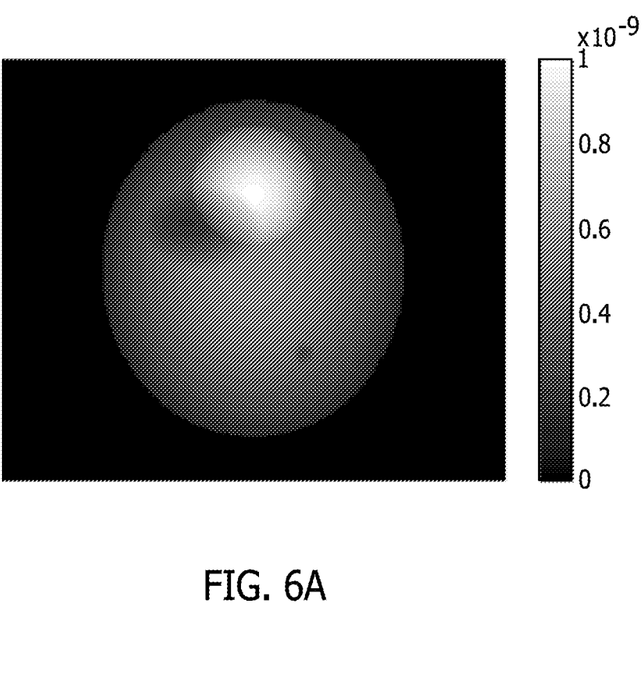
FIG. 6A is a computer-simulation result of reconstructed image of β, corresponding to an alternating aperture position (AAP)
Figure 6B:
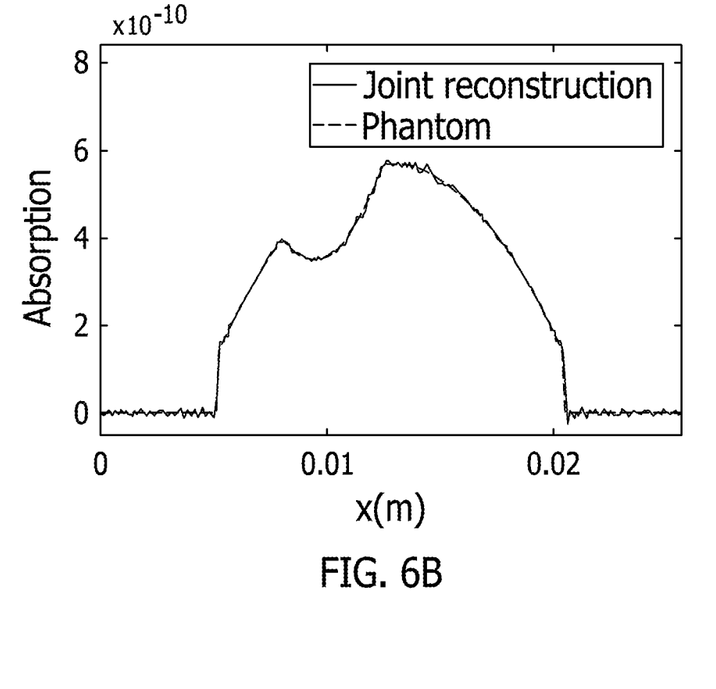
FIG. 6B is a graph of line profiles through the reconstructed image shown in FIG. 6A and corresponding true phantom shown in FIG. 4A.
Figure 6C:
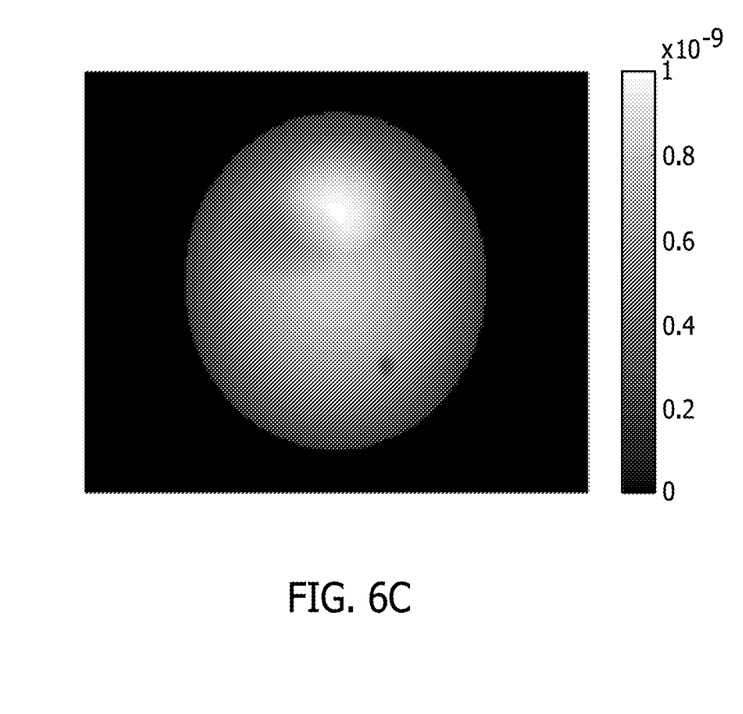
FIG. 6C is a computer-simulation result of reconstructed image of δ, corresponding to an AAP.
Figure 6D:
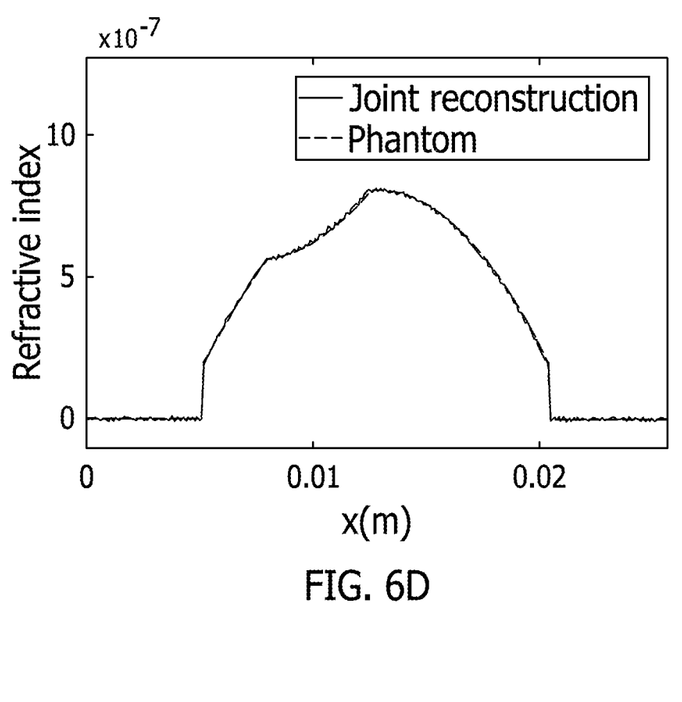
FIG. 6D is a graph of line profiles through the reconstructed image shown in FIG. 6C and corresponding true phantom shown in FIG. 4B.

Two distinct single-shot EIXPCT data sets were computed using the methodology described above. The first data set was a conventional single-shot data set in which aperture offset Δξ was constant at 720 evenly spaced tomographic view angles θ that spanned a 2π angular range, and aperture offset Δξ was set to 9.6 μm. Since this data set used a constant aperture position (CAP), it is referred to as the CAP data set. The second data set was non-conventional and its design was motivated by the flexibility of the joint reconstruction method 300, described above. The intensity data was collected at 360 evenly spaced tomographic view angles θ that spanned a π angular range. The aperture offset Δξ was not fixed and alternated between Δξ=9.6 μm and Δξ=−9.6 μm, changing value at each tomographic angle θ. Since this data set used an alternating aperture position (AAP), it is referred to as the AAP data set. The AAP data set addresses the situation when single-shot measurements are not available over a complete 2π range. FIGS. 5A and 5C show images of reconstructed estimates of β and δ, respectively, for the CAP data set. FIGS. 6A and 6C show images of reconstructed estimates of β and δ, respectively, for the AAP data set. Images were reconstructed from both data sets by use of Algorithm 1, described above, with no regularization (i.e., $p_1=p_2=0$). FIGS. 5B and 5D show line profiles through the reconstructed images of FIGS. 5A and 5C, respectively, and through the respective true phantom shown in FIGS. 4A and 4B. FIGS. 6B and 6D show line profiles through the reconstructed images of FIGS. 6A and 6C, respectively, and through the respective true phantom shown in FIGS. 4A and 4B.

The reconstructed images shown in FIGS. 5A and 6A are substantially the same as the numerical phantom image representing 3 shown in FIG. 4A, and the reconstructed images shown in FIGS. 5C and 6C are substantially the same as the numerical phantom image representing 8 shown in FIG. 4B. Additionally, the line profiles shown in FIGS. 5B, 5D, 6B, and 6D show that the line profiles across each phantom and respective reconstructed images are substantially the same.

The results of this example demonstrated the joint reconstruction algorithm reconstructs highly accurate images from idealized single-shot data. In particular, the results from the exemplary AAP data set show that a full 2n angular scanning range can be traded for a reduced scanning range of at least n if additional diversity in the measured data is created by varying aperture offset $\Delta\xi$ as a function of tomographic view angle θ.

Example 2: Joint Reconstruction of β and δ In Vivo

To further demonstrate the value of the joint reconstruction method 300 described above, in vivo image data from a previous experiment that used EIXPCT data sets was acquired. The image sample was a chicken bone, and the mean X-ray was 17 keV. As in the computer-simulated studies described above, intensity data was acquired at 720 view angles that were uniformly distributed over a 2π angular range. At each tomographic view angle θ, two intensity measurements were acquired corresponding to substantially symmetric positions on the illumination curve. An AAP data set was formed keeping either the measurement corresponding to the positive or negative side of the illumination curve, in an alternating fashion as a function of tomographic view angle θ.

Figure 7A:
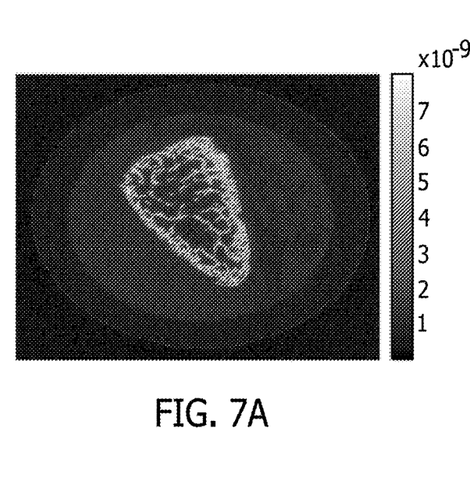
FIG. 7A is an estimate of β jointly reconstructed from an experimental data set using a CAP.
Figure 7B:
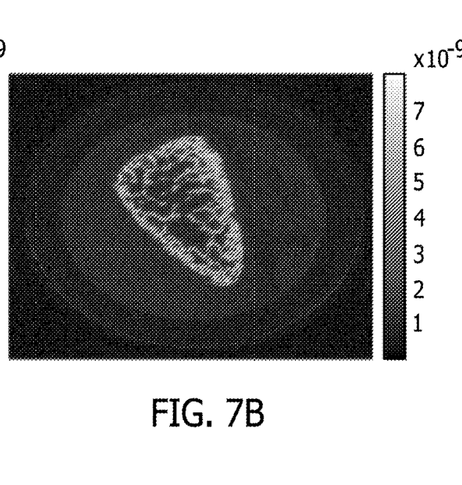
FIG. 7B is an estimate of β jointly reconstructed from an experimental data set using an AAP.
Figure 7C:
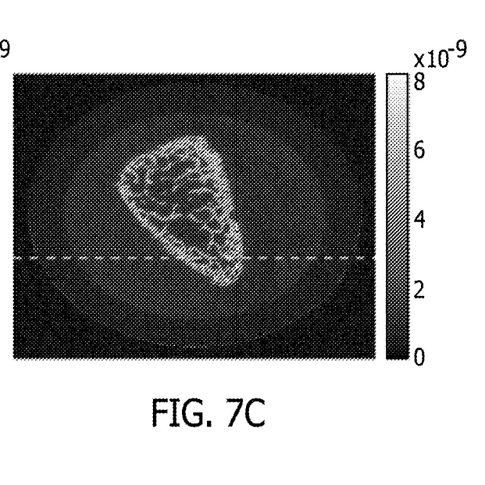
FIG. 7C is an estimate of β obtained by use of a conventional two-step, multi-shot method on an experimental data set.
Figure 7D:
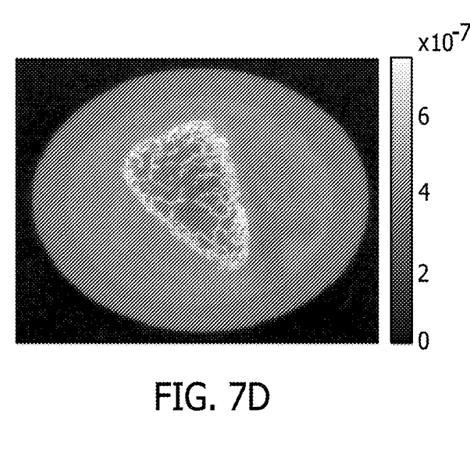
FIG. 7D is an estimate of δ jointly reconstructed from an experimental data set using a CAP.
Figure 7E:
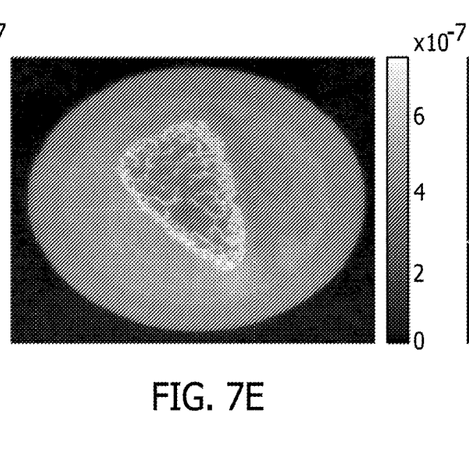
FIG. 7E is an estimate of δ jointly reconstructed from an experimental data set using an AAP.
Figure 7F:
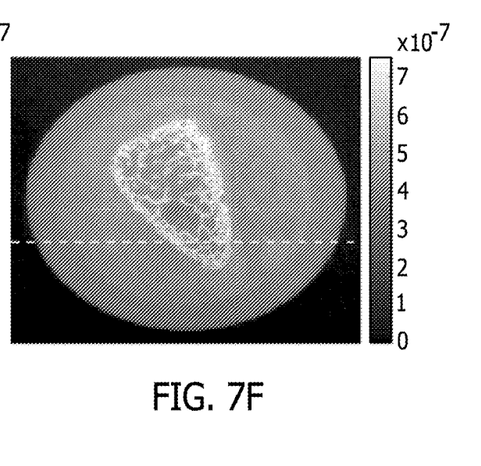
FIG. 7F is an estimate of δ obtained by use of a conventional two-step, multi-shot method on an experimental data set.

FIGS. 7A and 7D show images of estimates of β and δ, respectively, reconstructed from CAP data sets. FIGS. 7B and 7E show images of estimates of β and δ, respectively, reconstructed from AAP data sets. FIGS. 7C and 7F show images of estimates of β and 6, respectively, from conventional two-step method data sets. FIGS. 7A, 7B, 7D, and 7E were reconstructed using Algorithm 1. Penalty functions $R_\beta(\tilde{\beta})$ and $R_\delta(\tilde{\delta})$ were specified as a smoothed version of the total variation semi-norm. Suitable values of the regularization parameters $p_1$ and $p_2$ were manually determined and fixed for use with both data sets. FIGS. 7C and 7F were reconstructed by use of a conventional, non-single-shot approach in which both images acquired at each view angle were employed to perform phase-retrieval, followed by application of a filtered backprojection algorithm to determine estimates of β and δ.

Figure 8A:
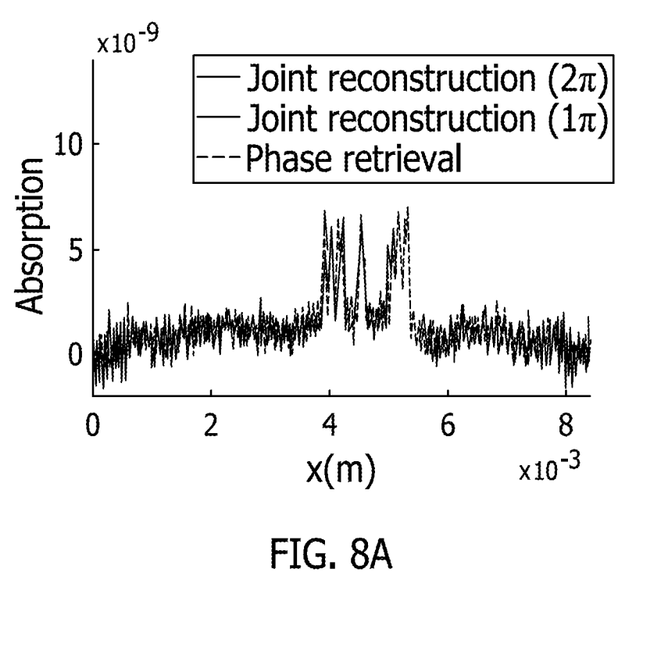
FIG. 8A is a graph of line profiles through the reconstructed images for all data acquisition plans corresponding to estimates of β at the white dashed line indicated in FIGS. 7C and 7F.
Figure 8B:
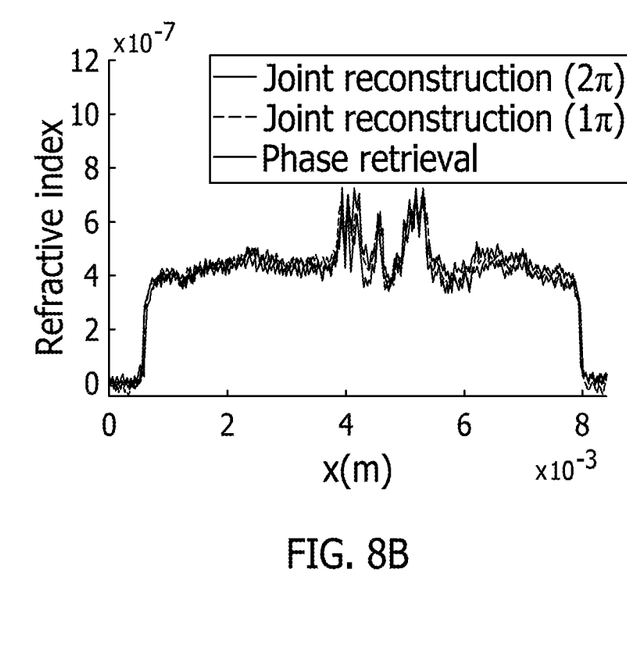
FIG. 8B is a graph of line profiles through the reconstructed images for all data acquisition plans corresponding to estimates of δ at the white dashed line indicated in FIGS. 7C and 7F.

FIG. 8A shows line profiles through each image shown in FIGS. 7A-C at the white dotted line shown in FIG. 7C, and FIG. 8B shows line profiles through each image shown in FIGS. 7D-F at the white dotted line shown in FIG. 7F. The line profiles shown in both FIG. 8A and FIG. 8B are nearly indistinguishable and show that each of the respective images are substantially the same.

The results of this experiment demonstrated that single-shot image reconstruction methods produce substantially similar images to images produced in the conventional two-shot approach, even in in vivo applications. In all of the images shown in FIGS. 7A-7F, the features of the chicken bone can be clearly identified. Further, as evident by the nearly overlapping line profiles shown in FIGS. 8A and 8B, the images reconstructed from both the CAP and AAP single-shot data sets by use of the joint reconstruction method are close in quantitative value to those reconstructed by use of the conventional two-step approach.

As used herein, a processor such as the processor 120 may include any programmable system including systems using micro-controllers, reduced instruction set circuits (RISC), application specific integrated circuits (ASICs), logic circuits, and any other circuit or processor capable of executing the functions described herein. The above examples are example only, and are thus not intended to limit in any way the definition and/or meaning of the term "processor."

As described herein, computing devices and computer systems include a processor and a memory. However, any processor in a computer device referred to herein may also refer to one or more processors wherein the processor may be in one computing device or a plurality of computing devices acting in parallel. Additionally, any memory in a computer device referred to herein may also refer to one or more memories wherein the memories may be in one computing device or a plurality of computing devices acting in parallel.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method of reconstructing a complex-valued X-ray refractive index distribution of an object having undergone X-ray phase-contrast tomography, the method comprising:
    acquiring at least one X-ray image of an object using an edge illumination X-ray phase-contrast tomography (EIXPCT) model derived from a 2-dimensional Radon transform, the at least one X-ray image including differential phase information;
    discretizing the EIXPCT model;
    jointly reconstructing the complex-valued refractive index distribution of the object using penalized least squares estimation of real and imaginary parts of the complex-valued refractive index distribution; and
    solving the penalized least squares estimation using a batch gradient algorithm.

2. The method of claim 1 further comprising reconstructing the image of the object for viewing by a subject.

3. The method of claim 1, wherein the at least one X-ray image is acquired from a plurality of view angles.

4. The method of claim 3, wherein acquiring the at least one X-ray image comprises utilizing varying aperture offset values over the plurality of view angles.

5. The method of claim 1, wherein solving the penalized least squares estimation using a batch gradient algorithm comprises:

calibrating an illumination curve;
retrieving measured X-ray intensity data from a memory;
initializing the penalized least squares estimation of estimation of the real and imaginary parts of the complex-valued refractive index distribution; and
iterating through specific criterion for an objective function value.

6. The method of claim 5, wherein iterating through the specific criterion for the objective function value is stopped when the objective function value falls below a specified threshold.

7. The method of claim 1, wherein jointly reconstructing the complex-valued refractive index distribution of the object using penalized least squares estimation is formulated as a numerical optimization problem.

8. An X-ray system for conducting edge illumination X-ray phase-contrast tomography (EIXPCT) on an object, the X-ray system comprising:
an image processing system comprising at least one processor coupled to a memory;
an X-ray source; and
an X-ray detector, wherein the image processing system, the X-ray source, and the X-ray detector are respectively communicatively coupled and configured in combination to:
acquire at least one X-ray image of an object using an edge illumination X-ray phase-contrast tomography (EIXPCT) model derived from a 2-dimensional Radon transform, the at least one X-ray image including differential phase information;
discretize the EIXPCT model;
jointly reconstruct a complex-valued refractive index distribution of the object using penalized least squares estimation of real and imaginary parts of the complex-valued refractive index distribution; and
solve the penalized least squares estimation using a batch gradient algorithm.

9. The X-ray system of claim 8, wherein the at least one X-ray image is acquired from a plurality of view angles.

10. The X-ray system of claim 9, wherein acquiring the at least one X-ray image comprises utilizing varying aperture offset values over the plurality of view angles.

11. The X-ray system of claim 10 further comprising a pre-sample mask and a detector mask, wherein the pre-sample mask is placed between the X-ray source and the object and wherein the detector mask is coupled to the X-ray detector.

12. The X-ray system of claim 11, wherein the differential phase information is obtained from moving the pre-sample mask by the varying aperture offset values.

13. The X-ray system of claim 8, wherein the image processing system, the X-ray source, and the X-ray detector are further configured in combination to reconstruct an image of the object for viewing by a subject.

14. An X-ray system for acquiring edge illumination X-ray phase-contrast tomography (EIXPCT) images of an object, the X-ray system comprising:
an X-ray source;
a pre-sample mask;
a detector mask; and
an X-ray detector system, wherein the acquired EIXPCT images of the object are processed by an image processing system coupled to the X-ray detector, and wherein the X-ray source, the pre-sample mask, the detector mask, the X-ray detector, and the image processing system are respectively communicatively coupled and configured in combination to:
acquire at least one X-ray image of an object from a plurality of view angles using an edge illumination X-ray phase-contrast tomography (EIXPCT) model derived from a 2-dimensional Radon transform, the at least one X-ray image including differential phase information;
discretize the EIXPCT model;
jointly reconstruct a complex-valued refractive index distribution of the object using penalized least squares estimation of real and imaginary parts of the complex-valued refractive index distribution; and
solve the penalized least squares estimation using a batch gradient algorithm.

15. The X-ray system of claim 14, the image processing system is further configured to reconstruct an image.

16. The X-ray system of claim 15, wherein the image processing system is further coupled to a display system configured to display the image that is reconstructed.

17. The X-ray system of claim 14, wherein the at least one X-ray image is acquired from a plurality of view angles.

18. The X-ray system of claim 17, wherein varying aperture offset values over the plurality of view angles are obtained by moving the pre-sample mask.

19. The X-ray system of claim 18, wherein the differential phase information is obtained from moving the pre-sample mask by the varying aperture offset values.

* * * * *